US012784879B2

(12) United States Patent
Min et al.

(10) Patent No.: US 12,784,879 B2
(45) Date of Patent: Nov. 3, 2026

(54) DEVICE AND METHOD FOR MODELING 2-DIMENSIONAL MATERIALS USING MACHINE LEARNING

(71) Applicant: FOUNDATION OF SOONGSIL UNIVERSITY-INDUSTRY COOPERATION, Seoul (KR)

(72) Inventors: Kyoung Min Min, Suwon-si (KR); In Hyo Lee, Seoul (KR); Joon Chul Kim, Seoul (KR)

(73) Assignee: FOUNDATION OF SOONGSIL UNIVERSITY-INDUSTRY COOPERATION, Seoul (KR)

( * ) Notice: Subject to any disclaimer, the term of this patent is extended or adjusted under 35 U.S.C. 154(b) by 478 days.

(21) Appl. No.: 18/523,079

(22) Filed: Nov. 29, 2023

(65) Prior Publication Data

US 2024/0282412 A1 Aug. 22, 2024

(30) Foreign Application Priority Data

Feb. 21, 2023 (KR) ........................ 10-2023-0022659

(51) Int. Cl.
*G16C 60/00* (2019.01)
*G06N 3/0455* (2023.01)
(Continued)

(52) U.S. Cl.
CPC ........... *G16C 60/00* (2019.02); *G06N 3/0455* (2023.01); *G06N 3/0475* (2023.01); *G16C 20/30* (2019.02); *G16C 20/70* (2019.02)

(58) Field of Classification Search
CPC ........ G16C 60/00; G16C 20/30; G16C 20/70; G16C 20/20; G16C 20/80; G06N 3/0455;
(Continued)

(56) References Cited

U.S. PATENT DOCUMENTS 11,004,037 B1 * 5/2021 Ling ...................... G06N 20/00
12,124,452 B1 * 10/2024 Chen .................. G06F 16/2455
(Continued)

FOREIGN PATENT DOCUMENTS

KR 10-2402582 B1 5/2022

OTHER PUBLICATIONS

Y. Song et al., "Computational Discovery of New 2D Materials Using Deep Learning Generative Models", ACS Appl. Mater. Interfaces vol. 13, pp. 53303-53313, May 14, 2021.
(Continued)

*Primary Examiner* — Timothy J Henn
(74) *Attorney, Agent, or Firm* — Bridgeway IP Law Group, PLLC; Jihun Kim

(57) ABSTRACT

A technology capable of finding new 2D materials with high elastic modulus and shear modulus through using deep learning, machine learning, and high-throughput calculation methods are described. A device for modeling 2-dimensional (2D) material using machine learning includes a material classification unit receiving data on the virtual inorganic material chemical formulas from the virtual inorganic material generation unit and classifying a 2D material among the plurality of virtual inorganic material chemical formulas into a preliminary 2D material, a space group analysis unit receiving data on the preliminary 2D material from the material classification unit, predicting the space group of the preliminary 2D material, and selecting the preliminary 2D material having the same space group as an existing 2D material as a structurally similar 2D material.

9 Claims, 8 Drawing Sheets

(51) Int. Cl.
*G06N 3/0475* (2023.01)
*G16C 20/30* (2019.01)
*G16C 20/70* (2019.01)

(58) Field of Classification Search
CPC ........ G06N 3/0475; G06N 3/045; G06N 3/08; G06N 5/01; G06N 20/20; G06N 3/044; G06N 3/094; G06N 20/10
See application file for complete search history.

(56) References Cited

U.S. PATENT DOCUMENTS

| | | | | |
|---|---|---|---|---|
| 2006/0074594 | A1* | 4/2006 | Ceder | G16C 20/30 702/182 |
| 2015/0154146 | A1* | 6/2015 | Yoo | G16C 20/50 702/181 |
| 2017/0124482 | A1* | 5/2017 | Yoo | G06N 20/00 |
| 2017/0193200 | A1* | 7/2017 | Hsu | G16C 20/30 |
| 2019/0171793 | A1* | 6/2019 | Aykol | G16C 20/10 |
| 2020/0227143 | A1* | 7/2020 | Katsuki | G06N 20/10 |
| 2020/0257933 | A1* | 8/2020 | Steingrimsson | B22F 5/04 |
| 2021/0081834 | A1* | 3/2021 | Hegde | G06N 3/0475 |
| 2021/0334655 | A1* | 10/2021 | Obika | G06N 3/08 |
| 2022/0044769 | A1* | 2/2022 | Ramprasad | G16C 20/70 |
| 2023/0315924 | A1* | 10/2023 | Hummelshøj | G06N 7/00 703/1 |
| 2024/0220683 | A1* | 7/2024 | Negoita | G06F 30/27 |
| 2025/0156692 | A1* | 5/2025 | Xie | G06N 3/096 |

OTHER PUBLICATIONS

E. Alibagheri et al., "Predicting the Electronic and Structural Properties of Two-Dimensional Materials Using Machine Learning", Computers, Materials & Continua vol. 67, pp. 1287-1300, Jan. 12, 2021.

* cited by examiner

| Index | Formula | Materials_id | Heat of formation [eV/atom] | Young's modulus (x direction) [N/m] | Young's modulus (y direction) [N/m] | Shear modulus (x-y plane) [N/m] |
|---|---|---|---|---|---|---|
| 1 | $Si_2F_8$ | 2dm-2460 | -3.079 | 788.877 | 1629.341 | 133.542 |
| 2 | $NbO_2$ | 2dm-2606 | -1.781 | 1419.338 | 265.976 | 7.550 |
| 3 | $NbO_2$ | 2dm-2415 | -1.781 | 1407.497 | 266.380 | 8.014 |
| 4 | $NbO_2$ | 2dm-2663 | -1.779 | 1381.748 | 263.195 | 7.151 |
| 5 | $Mg_2P$ | 2dm-1862 | -0.262 | 738.736 | 735.369 | 124.021 |

FIG. 4

DEVICE AND METHOD FOR MODELING 2-DIMENSIONAL MATERIALS USING MACHINE LEARNING

CROSS REFERENCE TO RELATED APPLICATION

The present application claims priority to Korean Patent Application No. 10-2023-0022659, filed Feb. 21, 2023, the entire contents of which is incorporated herein for all purposes by this reference.

BACKGROUND OF THE INVENTION

Field of the Invention

The present invention relates to a device and method for modeling 2-dimensional (2D) materials using machine learning, and more particularly, to a technology capable of discover new 2D materials with high elastic modulus and shear modulus through deep learning, machine learning, and high-throughput calculation.

Description of the Related Art

A 2D material refers to a substance with a thin thickness measured in nanometers. 2D materials have excellent electrical and chemical properties, as well as the advantages of being flexible and optically transparent, which are derived from their thin thickness.

For example, graphene has a high elastic modulus of around 1 TPa and exhibits excellent electrical conductivity, making it a highly conductive material. Single layer of MoS has a direct bandgap of approximately 1.8 eV and exhibits high luminescence efficiency.

Phase-change random-access memory (PRAM) made of 2D MoTe2 has the advantage of being faster in data storage and retrieval speed than those made of conventional materials. The properties of each 2D material suggest the possibility of applying 2D materials to a variety of industries, including next-generation displays, solar energy, the aerospace industry, and semiconductors.

However, commercializing these 2D materials remains a challenging problem. The difficulty lies in achieving mass production of widely known 2D materials, using mechanical exfoliation and chemical vapor deposition methods, without compromising their excellent properties. Furthermore, the unique properties of each 2D material pose difficulties in terms of their commercialization.

For example, graphene possesses strong bonding forces between its constituent atoms, making it difficult to bond with other materials. MoS is also the same. Furthermore, these materials have the disadvantage of being prone to oxidation, which results in the electrical properties being easily altered.

Therefore, in addition to existing 2D materials, finding new 2D materials that are easy to synthesize plays a very important role in the development of various industrial fields. Furthermore, in the commercialization of 2D materials, structural stability is an important criterion for assessment. The material must be highly resistant to external forces such as tension, compression, and fracture, as well as resistance to damage and breakage. For these reasons, the discovery of new 2D materials with high elastic modulus and shear modulus holds significant industrial value.

On the other hand, using traditional experimental methods to discover such 2D materials would lead to inefficient results in terms of time and cost. This is due to the inevitable trial and error process and the uncertainty regarding the synthesis feasibility of new 2D materials. Additionally, there is a drawback of being highly influenced by changes in experimental conditions.

The Korean registered patent No. 10-2402582 (invention name: Electronic device that generates chemical structural formulas for new drug development based on a machine learning-based chemical generation model and the operating method thereof) discloses an electronic device including a training set storage unit in which multiple chemical structural formulas represented by SMILES notation are stored as a training set; a first correction unit that selects one of the multiple chemical structural formulas as a first chemical structural formula, appends a start character to the front of the first chemical structural formula and appends an end character to the end of the first chemical structural formula to correct the first chemical structural formula; a first character pair generation unit that, upon completion of the correction of the first chemical structural formula, generates multiple first character pairs corresponding to the corrected first chemical structural formula by sequentially designating a character located at the $n^{th}$ position (where n is a natural number greater than or equal to 1) in the string composing the corrected first chemical structural formula as input and designating the character located at the $(n+1)^{th}$ position as the answer, a first vector verification unit that refers to the vector storage unit to verify embedding vectors for characters specified as inputs in the multiple first character pairs; and a first probability value generation unit that, for each of the multiple first character pairs, sequentially matches them to multiple time steps of a recurrent neural network (RNN), inputs the embedding vector for the character specified as input in each character pair to the matched time step, and calculates probability values indicating the likelihood of the character designated as the answer in each character pair being produced using predetermined activation functions for each time step matched to each character pair, based on the start character, end character, and multiple characters stored in the character storage unit.

DOCUMENTS OF RELATED ART (Patent Document 1) Korean Patent Registration No. 10-2402582

SUMMARY OF THE INVENTION

The present invention has been conceived to solve the above problems and it is an object of the present invention to provide a technology that is capable of finding new 2D materials with high elastic modulus and shear modulus through the use of deep learning, machine learning, and high-throughput calculation methods.

The technical objects of the present invention are not limited to the aforesaid, and other objects not described herein with can be clearly understood by those skilled in the art from the descriptions below.

In order to accomplish the above objects, a device of the present invention includes a virtual inorganic material generation unit generating a plurality of virtual inorganic material chemical formulas, a material classification unit receiving data on the virtual inorganic material chemical formulas from the virtual inorganic material generation unit and classifying a 2D material among the plurality of virtual inorganic material chemical formulas into a preliminary 2D material, a space group analysis unit receiving data on the preliminary 2D material from the material classification unit, predicting the space group of the preliminary 2D material, and selecting the preliminary 2D material having the same space group as an existing 2D material as a structurally similar 2D material, a similarity analysis unit receiving data on the structurally similar 2D material from the space group analysis unit and deriving the structurally similar 2D material having a similar chemical composition to the existing 2D material as a compositionally similar 2D material, and a new material generation unit receiving data on the compositionally similar 2D material from the similarity analysis unit and deriving a new 2D material by performing element substitution between chemical formulas of the compositionally similar 2D material and the existing 2D material matching the compositionally similar 2D material.

In an embodiment of the present invention, the virtual inorganic material generation unit may generate the virtual inorganic material chemical formulas using a generative adversarial network (GAN).

In an embodiment of the present invention, the material classification unit may select the preliminary 2D material using a random forest model.

In an embodiment of the present invention, the material classification unit may train the random forest model using a virtual material database as predefined material data.

In an embodiment of the present invention, the space group analysis unit may predict the space group of the preliminary 2D material using a neural network (NN).

In an embodiment of the present invention, the similarity analysis unit may analyze the chemical similarity of the existing 2D material and the structurally similar 2D material using a distance function.

In an embodiment of the present invention, the distance function may be the earth mover's distance (EMD) function.

In an embodiment of the present invention, the device may further include a property analysis unit receiving data on the new 2D material from the new material generation unit and computing thermodynamic stability and mechanical property of the new 2D material.

In an embodiment of the present invention, the property analysis unit may perform density functional theory (DFT) calculation on the new 2D material and removes the new 2D material having a negative value for the stiffness tensor among a plurality of types of new 2D materials.

In an embodiment of the present invention, the device may further include a display unit displaying information on the new 2D material received from the property analysis unit on a screen.

In order to accomplish the above objects, a method of the present invention includes generating a plurality of virtual inorganic material chemical formulas; classifying a 2D material among the plurality of virtual inorganic material chemical formulas into a preliminary 2D material using data on the virtual inorganic material chemical formulas; predicting the space group of the preliminary 2D material and selecting the preliminary 2D material having the same space group as an existing 2D material as a structurally similar 2D material; deriving the structurally similar 2D material having a similar chemical composition to the existing 2D material as a compositionally similar 2D material; and deriving a new 2D material by performing element substitution between chemical formulas of the compositionally similar 2D material and the existing 2D material matching the compositionally similar 2D material.

BRIEF DESCRIPTION OF THE DRAWINGS

FIG. 4 is a table listing materials derived by a modeling device according to an embodiment of the present invention;

DETAILED DESCRIPTION OF THE INVENTION

Figure 1:
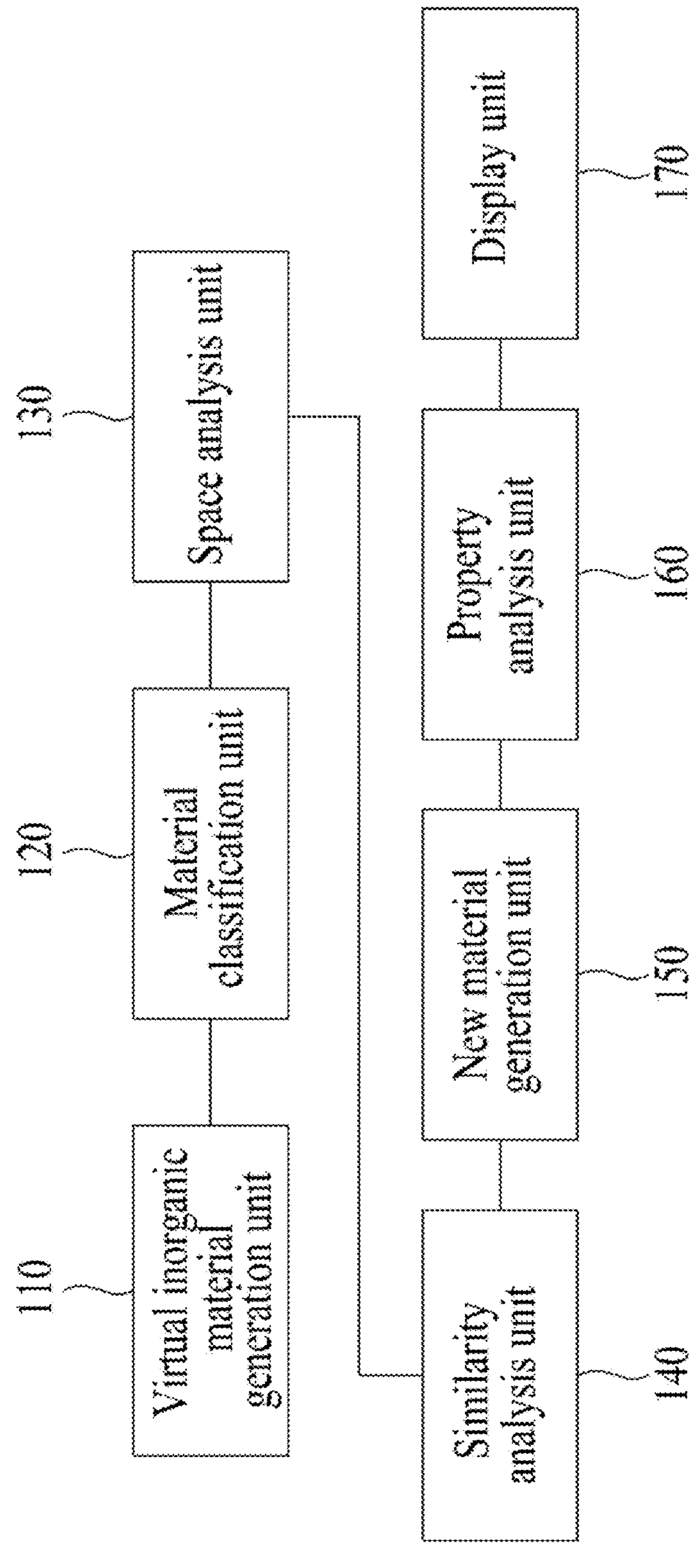
FIG. 1 is a block diagram illustrating a configuration of a modeling device according to an embodiment of the present invention.

Hereinafter, the present invention will be described with reference to the accompanying drawings. However, the present invention may be embodied in many different forms and is not limited to the embodiments described herein. In order to clearly describe the present invention, parts irrelevant to the description may be omitted in the drawings, and similar reference numerals may be used for similar components throughout the specification.

Throughout the specification, when a part is said to be "connected (coupled, contacted, or combined)" with another part, this is not only "directly connected", but also "indirectly connected" with another member in between. Also, when a part is said to "comprise" a certain component, this means that other components may be further included instead of excluding other components unless specifically stated otherwise.

The terminology used herein is for the purpose of describing particular embodiments only and is not intended to be limiting of the invention. As used herein, the singular forms are intended to include the plural forms as well, unless the context clearly indicates otherwise. It will be further understood that the terms "comprises" or "has," when used in this specification, specify the presence of a stated feature, number, step, operation, component, element, or a combination thereof, but they do not preclude the presence or addition of one or more other features, numbers, steps, operations, components, elements, or combinations thereof.

Hereinafter, the present invention will be described in detail with reference to the accompanying drawings.

FIG. 1 is a block diagram illustrating a configuration of a modeling device according to an embodiment of the present invention.

As shown in FIG. 1, the modeling device of the present invention includes a virtual inorganic material generation unit 110 that generates a plurality of virtual inorganic chemical formulas; a material classification unit 120 that receives the data of virtual inorganic chemical formulas from the virtual inorganic material generation unit 110 and classifies 2D materials among the plurality of virtual inorganic materials into preliminary 2D materials; a space group analysis unit 130 that receives the data on preliminary 2D materials from the material classification unit 120, predicts their space groups of the preliminary 2D materials, and selects the preliminary 2D materials having the same space group as existing 2D materials as structurally similar 2D materials; a similarity analysis unit 140 that receives the data on structurally similar 2D materials from the space group analysis unit 130 and identifies the structurally similar 2D materials having similar in chemical composition to the existing 2D materials with the same space group as compositionally similar 2D materials; and a new material generation unit 150 that receives the data on compositionally similar 2D materials from the similarity analysis unit 140 and performs element substitution between the chemical formulas of the compositionally similar 2D materials and the existing 2D materials matching the compositionally similar 2D material to derive new 2D materials.

Each of the virtual inorganic material generation unit 110, material classification unit 120, space group analysis unit 130, similarity analysis unit 140, and new material generation unit 150, and a subsequent property analysis unit 160 to be described later may be implemented using hardware such as a computer or central processing units (CPU), software such as an operating program, or a combination of both. In addition, one unit may be implemented using two or more hardware components, and two or more units may also be implemented using a single hardware component.

The virtual inorganic material generation unit 110 may generate virtual inorganic chemical formulas using generative adversarial networks (GAN). In detail, the virtual inorganic material generation unit 110 may use a generative deep learning model for inorganic materials (MatGAN) trained on inorganic chemical formulas, which is capable of generating over one million virtual inorganic chemical formulas.

In an embodiment of the present invention, it is possible to generate 1,450,283 virtual inorganic chemical formulas.

The MatGAN Generator is a Python-based platform that can be obtained through open-source websites, and the acquired program is stored in the virtual inorganic material generation unit 110 for use in generating a plurality of virtual inorganic chemical formulas as described above.

The material classification unit 120 may use a random forest model (RF) for the selection of preliminary 2D materials. The material classification unit 120 may also train the RF model using a virtual material database as the predefined material data.

The material classification unit 120 may screen preliminary 2D materials from the plurality of virtual inorganic materials to form a set of candidates for 2D materials, called the 2D material candidate group, and a set of materials not suitable for preliminary 2D materials, called the non-2D material group.

To accomplish this, the material classification unit 120 may first train the random forest model using an existing virtual material database, which be obtained from the Materials Project (MP) and the 2D Materials Encyclopedia (2DMatPedia) websites, respectively.

The random forest (RF) model is effective in processing large amounts of data and robust to data imbalance. In the virtual material database, the database obtained from the Materials Project (MP) may be referred to as the first data, and the database obtained from the 2D Materials Encyclopedia (2DMatPedia) may be referred to as the second data.

Here, the first data may include the chemical formulas of other materials other than 2D materials, and the second data may include the chemical formulas of 2D materials. In an embodiment, the first data may consists of 126,631 entries while the second data may include 6,351 entries. However, the numbers of entries are not necessarily limited thereto.

When the first data and the second data are input into the material classification unit 120, the material classification unit 120 may generate non-2D training data for the chemical formula of materials other than 2D materials in the first data by excluding the second data from the first data, and 2D training data using the second data as training data for 2D materials.

The material classification unit 120 may train the random forest (RF) model using both the 2D training data and the non-2D training data. Here, the number of chemical formulas in the non-2D training data may be approximately 19 times larger than the number of chemical formulas in the 2D training data.

Figure 2:
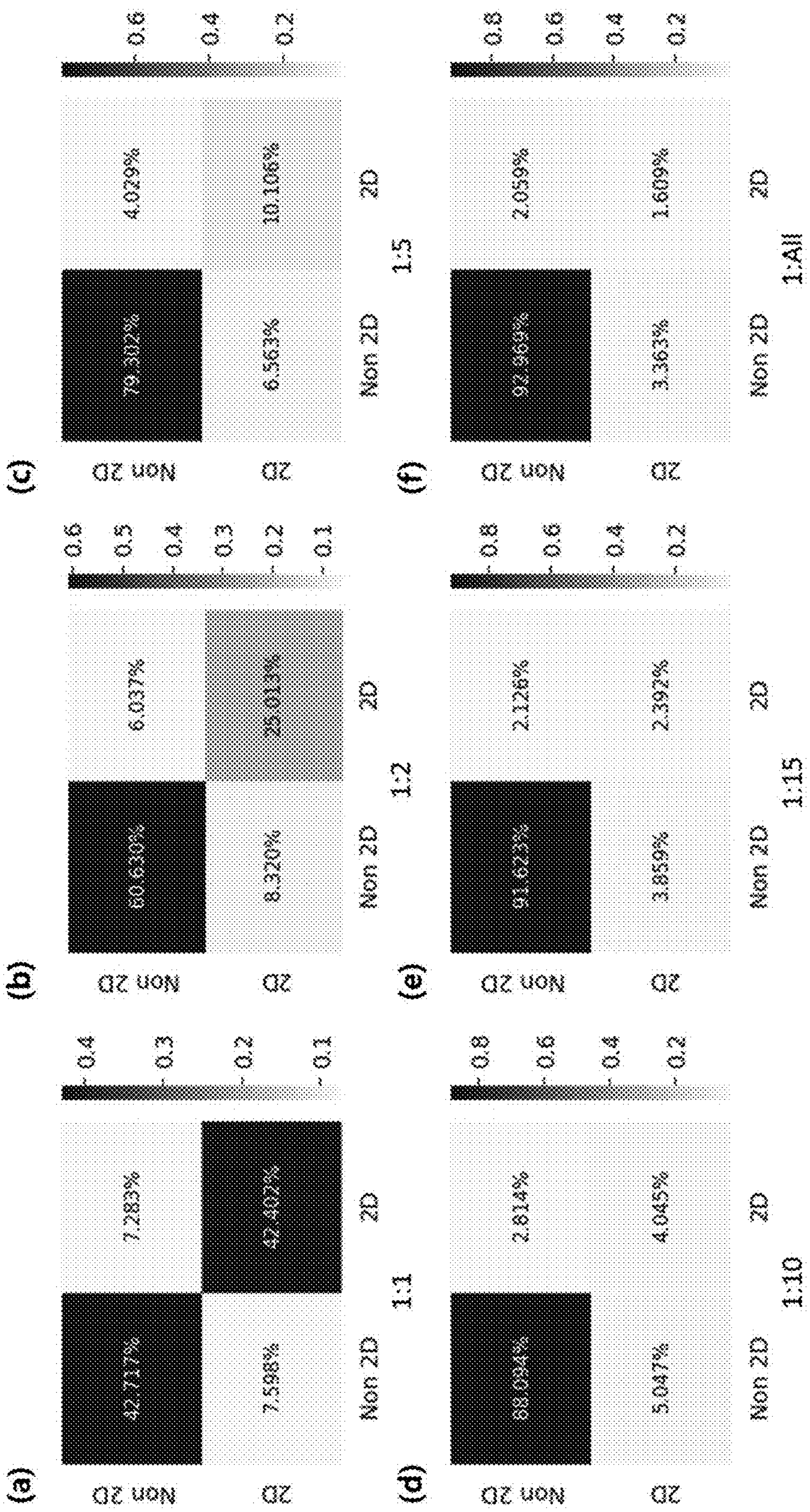
FIG. 2 is a diagram representing performance analysis of a material classification unit according to an embodiment of the present invention.

FIG. 2 is a diagram representing performance analysis of a material classification unit according to an embodiment of the present invention. In detail, FIG. 2 illustrates confusion matrices showing the performances of the random forest (RF) model depending on the changes in the 2D training data and non-2D training data as training data sets and, in FIG. 2, "2D" may represent 2D training data and "non 2D" may represent non-2D training data.

Here, part (a) in FIG. 2 represents the case where the ratio of 2D training data to non-2D training data is 1:1, part (b) of FIG. 2 represents the case where the ratio is 1:2, part (c) of FIG. 2 represents the case where the ratio is 1:5, part (d) of FIG. 2 represents the case where the ratio is 1:10, part (e) of FIG. 2 represents the case where the ratio is 1:15, and part (f) of FIG. 2 represents the case where all available data is used for training without a specific ratio between 2D and non-2D training data.

As shown in FIG. 2, the material classification unit 120 may search for the optimal ratio of 2D to non-2D training data by utilizing down-sampling techniques for the number of non-2D training data during the training process of the random forest (RF) model.

Here, when the ratio of 2D to non-2D training data is 1:1, the performance metrics of precision, recall, f1-score, and accuracy for the random forest (RF) model may be analyzed to be approximately 0.850, which is the highest; thus, the material classification unit 120 may perform training using the random forest (RF) model with a ratio of 1:1 for 2D and non-2D training data.

Although the description is focused on the machine learning being performed in the material classification unit 120 by generating 2D training data and non-2D training data using the first data and the second data in an embodiment of the present invention, the performance metrics may be changed by changing the data.

The material classification unit 120 may store a performance metric threshold value (decision threshold) of 0.9 for the random forest (RF) model, and when setting the ratio of 2D to non-2D training data as described above, the ratio of 2D to non-2D training data may be adjusted to match the performance metrics of the random forest (RF) model that are close to 0.9.

Figure 3:
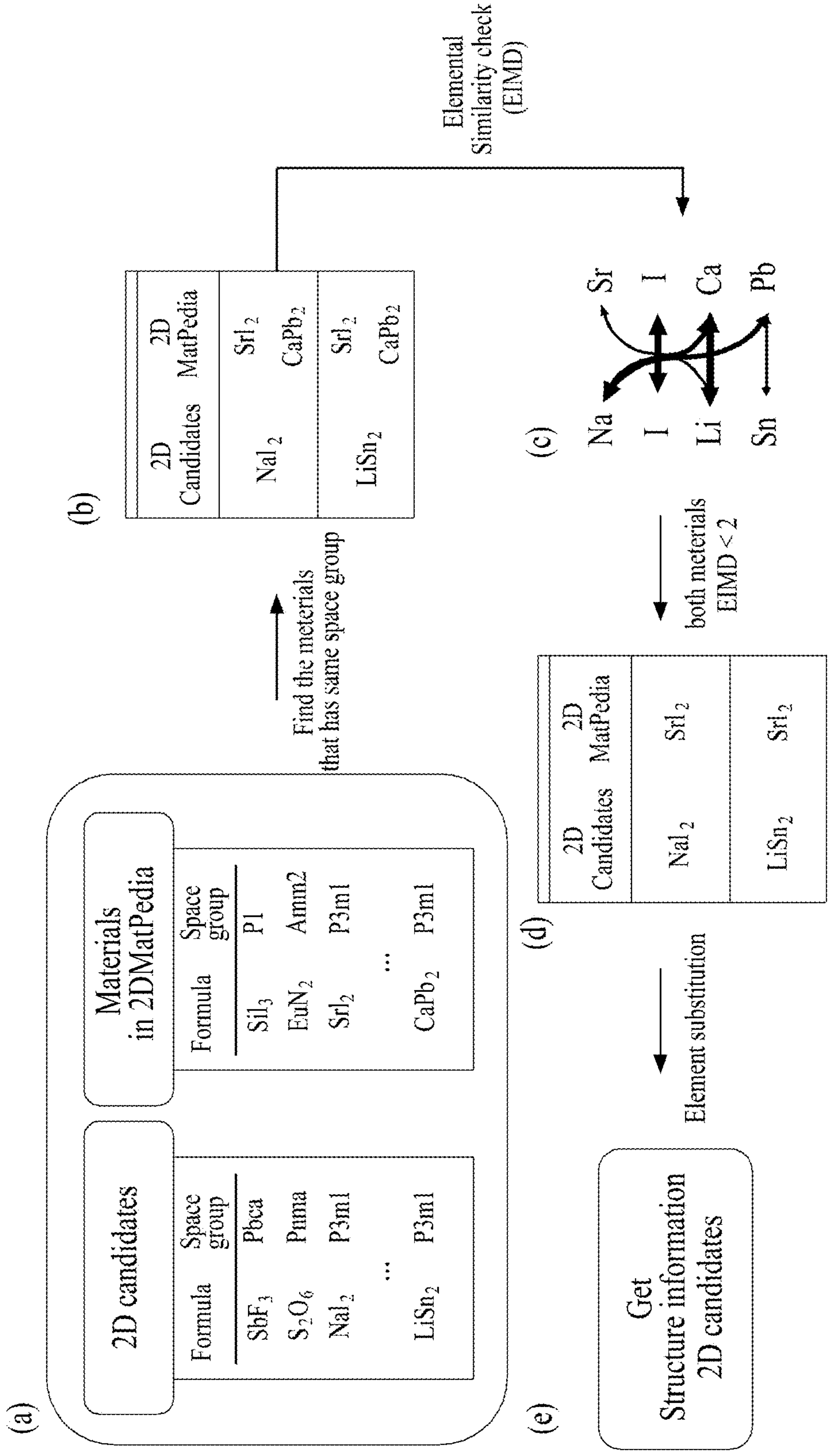
FIG. 3 is a diagram illustrating a flow sequence of screening conducted in a spatial analysis unit, similarity analysis unit, and new material generation unit according to an embodiment of the present invention.

FIG. 3 is a diagram illustrating a flow sequence of screening conducted in a spatial analysis unit 130, similarity analysis unit 140, and new material generation unit 150 according to an embodiment of the present invention.

As shown in FIG. 3, based on the operation of the space group analysis unit 130 and the similarity analysis unit 140, structural and elemental similarity-based screening may be performed on the 2D materials classified preliminarily by the material classification unit 120.

Here, part (a) of FIG. 3 shows information about the formula and space group of the preliminary 2D materials on the left side (2D candidates) and information about the chemical formula and space group of the 2D materials within the second data on the right side (Materials in 2DMatPedia).

Part (b) of FIG. 3 shows NaI2 and LiSn2 as structurally similar 2D candidates, which are preliminary 2D materials selected by the spatial analysis unit 130, and SrI2, CaPb2, SrI2, and CaPb2 as existing 2D materials having the same space group as the structurally similar 2D materials.

Part (c) of FIG. 3 shows the analysis of chemical composition similarity performed by the similarity analysis unit 140, part (d) of FIG. 3 shows the compositionally similar 2D candidates (2D candidates) selected by the similarity analysis unit 140 and the corresponding existing 2D materials (2D MetPedia). Part (e) of FIG. 3 shows the derivation of new 2D materials through element substitution in the new material generation unit 150.

The space group analysis unit 130 may predict the space group of preliminary 2D materials using an artificial neural network (NN). As shown in part (a) of FIG. 3, the space group of the second data may be used for space group analysis of existing 2D materials in the space group analysis unit 130.

Upon receiving the data about the preliminary 2D materials, the space analysis unit 130 may perform predictions for the space group of each preliminary 2D material included in the data using crystal structure predictions via neural network (CRYSPNet) and the data about the preliminary 2D materials.

CRYSPNet, which is an engine for use in predicting the crystal structure of inorganic material using a neural network (NM), is a tool (program) capable of predicting the Bravais lattice, space group, and lattice parameters of inorganic materials.

CRYSPNet is a platform based on Python and other programming languages, which may be obtained through open-source websites or similar sources, and once acquired, the program may be stored in the space group analysis unit 130 for use by the space group analysis unit 130 in performing space group predictions for the preliminary 2D materials.

As described above, the space group analysis unit 130 may perform space group predictions on the preliminary 2D materials and compare the predicted space groups of the preliminary 2D materials with the space groups of the existing 2D materials in the second data to match and classify the preliminary 2D materials with the same space group as the existing 2D materials.

Accordingly, based on the matching performed by the space group analysis unit 130, the preliminary 2D materials having the same space group as the existing 2D materials may be classified, and data for structurally similar 2D materials may be generated.

In the space group analysis unit, it is possible for one structurally similar 2D material to match with one existing 2D material among multiple existing 2D materials. Here, as shown in part (b) of FIG. 3, there may be a plurality of existing 2D materials (2D MetPedia) that match with one structurally similar 2D material (2D candidates).

Part (b) of FIG. 3 shows SrI2 and CaPb2 as existing 2D materials with the same space group as NaI2 that is a structurally similar 2D material, and SrI2 and CaPb2 as existing 2D materials with the same space group as LiSn2 that is a structurally similar 2D material.

After the analysis in the space group analysis unit 130, the data on the structurally similar 2D materials and the data on the existing 2D materials with the same space group as the structurally similar 2D materials may be transmitted from the space group analysis unit 130 to the similarity analysis unit 140.

The similarity analysis unit 140 may analyze the chemical similarity between the existing 2D materials and the structurally similar 2D materials using a distance function. Here, the distance function may be the earth mover's distance function (EMD).

In detail, the Earth Mover's Distance (EMD) function may be used to compute the distance between the constituents of 2D materials, and an operational program called element mover distance (EIMD) may be developed using EMD for such calculations.

The similarity analysis unit 140 may utilize the data on structurally similar 2D materials, the data on existing 2D materials with the same space group as the structurally similar 2D materials, and the EIMD to derive the EIMD result values for the structurally similar 2D materials and the existing 2D materials with the same space group as the structurally similar 2D materials.

EIMD is a Python-based library used to measure the chemical similarity between two materials, and it may obtained from open-source sites and stored in the similarity analysis unit 140, allowing the similarity analysis unit 140 to compute EIMD result values between structurally similar 2D materials and existing 2D materials with the same space group.

The similarity analysis unit 140 may derive the EIMD result value for the structurally similar 2D materials and the existing 2D materials with the same space group and may determine whether the EIMD result value is less than a threshold value.

Here, the lower the EIMD result value, the more similar the compositions of the constituent elements between the structurally similar 2D materials and the existing 2D materials with the same space group. Here, the threshold value may be 2, but is not limited thereto, and the benchmark value may be changed.

The similarity analysis unit 140 may determine whether the EIMD result value between one of a plurality of structurally similar 2D materials and at least one existing 2D material with the same space group as the corresponding structurally similar 2D material is less than the threshold value.

As shown in part (d) of FIG. 3, the similarity analysis unit 140 may classify and select a set of structurally similar 2D materials and existing 2D materials with the same space group by matching the materials when the EIMD result value is less than the threshold value.

The structurally similar 2D materials included in the set classified in the above manner may be called compositionally similar 2D materials, and the existing 2D materials that match the compositionally similar 2D materials in in the set may be referred to as substitutional 2D materials.

The new material generation unit 150 may receive data on compositionally similar 2D materials and substitutional 2D materials from the similarity analysis unit 140 and derive the chemical formula of a new 2D material from the compositionally similar 2D material by substituting the constituent elements of one compositionally similar 2D material and one substitutional 2D material in a 1:1 ratio.

The modeling device of the present invention may further include a property analysis unit 160 that receives data on the new 2D material from the new material generation unit 150 and computes the thermodynamic stability and mechanical properties of the new 2D material.

The property analysis unit 160 may perform density functional theory (DFT) calculations on the new 2D material to remove the new 2D material with a negative value of the stiffness tensor from a plurality of types of new 2D materials.

In detail, the property analysis unit 160 may perform density functional theory (DFT) calculations using a simulation program, and the simulation program stored in the property analysis unit 160 may be Vienna ab initio simulation package (VASP).

During the process of performing density functional theory (DFT) calculations in the property analysis unit 160, the structural stabilization of the new 2D material formed through element substitution may be performed, and the thermodynamic stability and mechanical properties of the new 2D material may be calculated.

In order to consider reality, the property analysis unit 160 may derive the stiffness tensor of the new 2D materials through density functional theory (DFT) calculations and selectively remove the new 2D materials with negative values of the stiffness tensor from the data.

FIG. 4 is a table listing materials derived by a modeling device according to an embodiment of the present invention. In an embodiment of the present invention, 554 new 2D materials were finally selected, and FIG. 4 shows the top 5 new 2D materials, which are thermodynamically stable and have high average values of elastic modulus and shear modulus, along with their properties.

The modeling device of the present invention may further includes a display unit 170 displaying information about the new 2D materials on a screen. The display unit 170 may receive information on the new 2D material from the property analysis unit 160 and display information on the crystal structure, mechanical properties, etc. of the new 2D material on the screen in the form of images, text, and the like.

Figure 5:
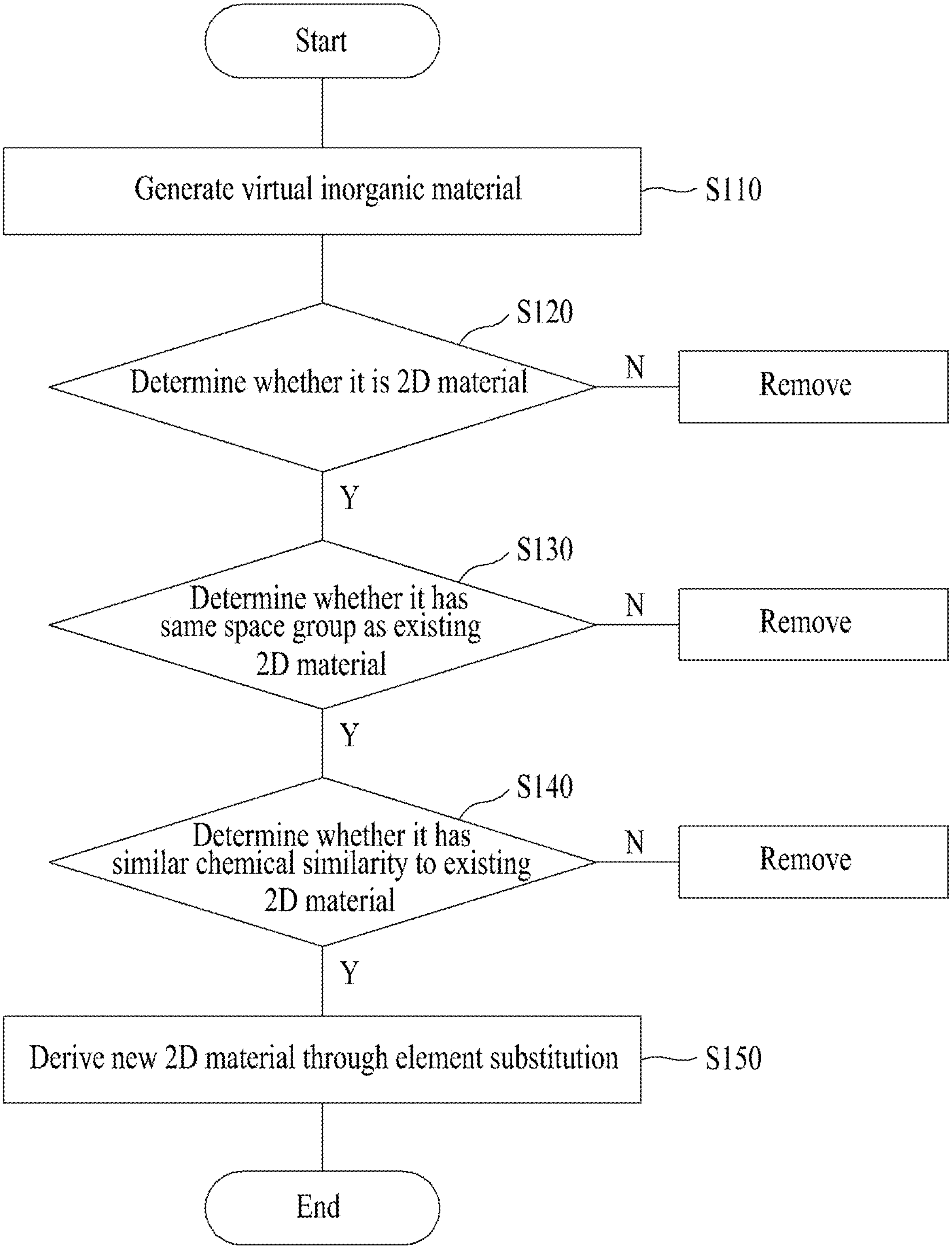
FIG. 5 is a flowchart illustrating a modeling method according to an embodiment of the present invention.

FIG. 5 is a flowchart illustrating a modeling method according to an embodiment of the present invention. Hereinafter, a description is made of the modeling method of present invention.

First, it is possible to generate a plurality of inorganic chemical formulas at step S110. As described above, step S110 may be performed by the virtual inorganic material generation unit 110.

Next, it is possible to classify a preliminary 2D material among a plurality of virtual inorganic materials at step S120 using data on the virtual inorganic chemical formulas. As described above, step S120 may be performed by the material classification unit 120.

In detail, the material classification unit 120 may analyze a virtual inorganic material to determine at step S120 whether the virtual inorganic materials is a 2D material, classify the virtual inorganic material as a preliminary 2D material based on the virtual inorganic material being a 2D material, and remove the virtual inorganic material from the data based on the virtual inorganic material being not a 2D material.

Next, it is possible to predict the space group of the preliminary 2D material and select the preliminary 2D material as a structurally similar 2D material based on the preliminary 2D material having the same space group as an existing 2D material at step S130. As described above, step S130 may be performed by the space group analysis unit 130.

In detail, the space group analysis unit 130 compares the predicted space group of the preliminary 2D material with the space group of the existing 2D material at step S130 to classify the preliminary 2D material into a structurally similar 2D material based on the preliminary 2D material having the same space group as the existing 2D material and remove the preliminary 2D material from the data based on the preliminary 2D material not having the same space group as the existing 2D material.

Next, it is possible to derive the structurally similar 2D material as a compositionally similar 2D material based on the structurally similar 2D material having a similar chemical composition to the existing 2D material with the same space group at step S140. As described above, step S140 may be performed by the similarity analysis unit 140.

In detail, the similarity analysis unit 140 may determine at step S140 whether the existing 2D material and the structurally similar 2D material having the same space group have the chemical composition similarity, i.e., chemical similarity, to classify the structurally similar 2D material into a compositionally similar 2D material based on the structurally similar 2D material and the existing 2D material being chemically similar and remove the structurally similar 2D material from the data based on the structurally similar 2D material and the existing 2D material being not similar chemically.

Next, it is possible to derive a new 2D material at step S150 by performing element substitution between the chemical formulas of the compositionally similar 2D material and the existing 2D material. As described above, step S150 may be performed by the new material generation unit 150.

The remaining detailed aspects of the modeling method of the present invention are the same as those described in the modeling device of the present invention.

Figure 6:
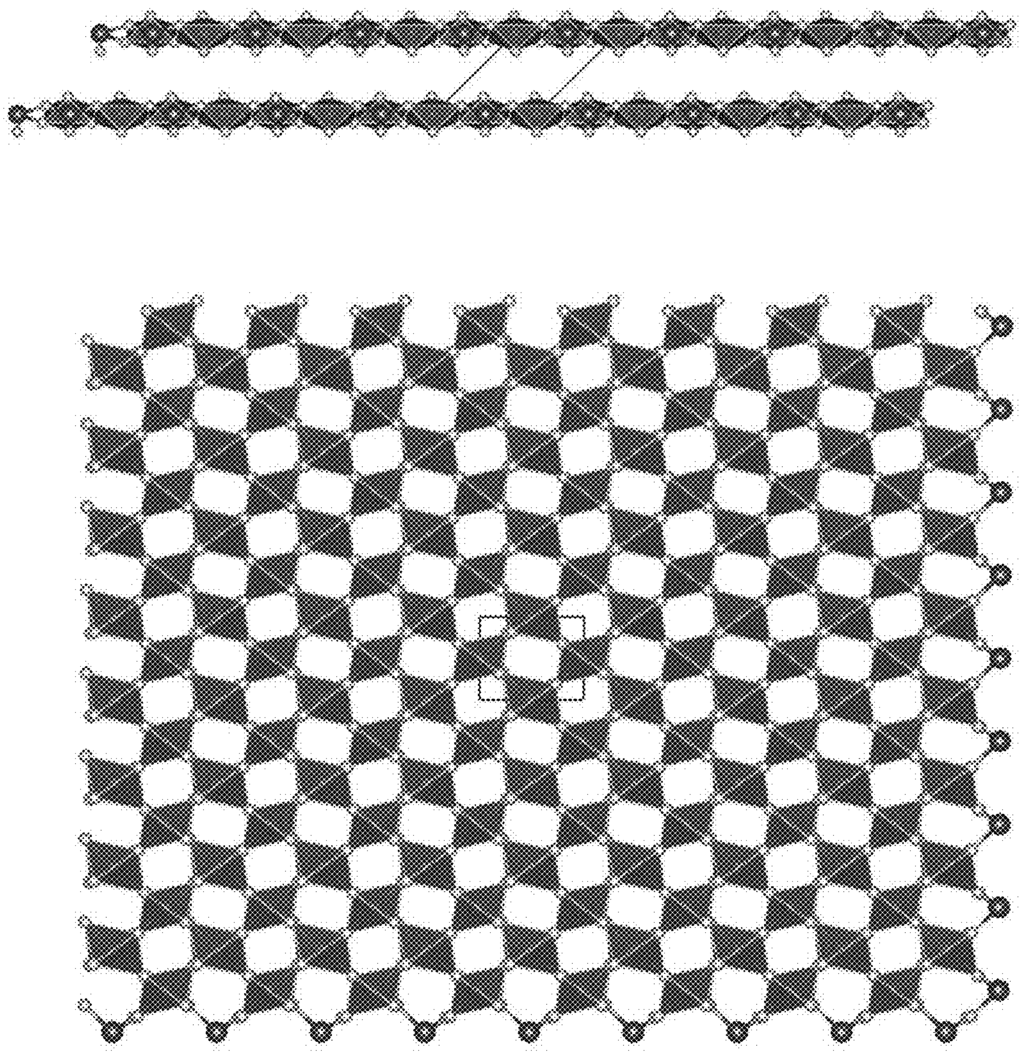
FIGS. 6 to 8 are images depicting the crystal structures of materials derived by a modeling device according to an embodiment of the present invention.
Figure 7:
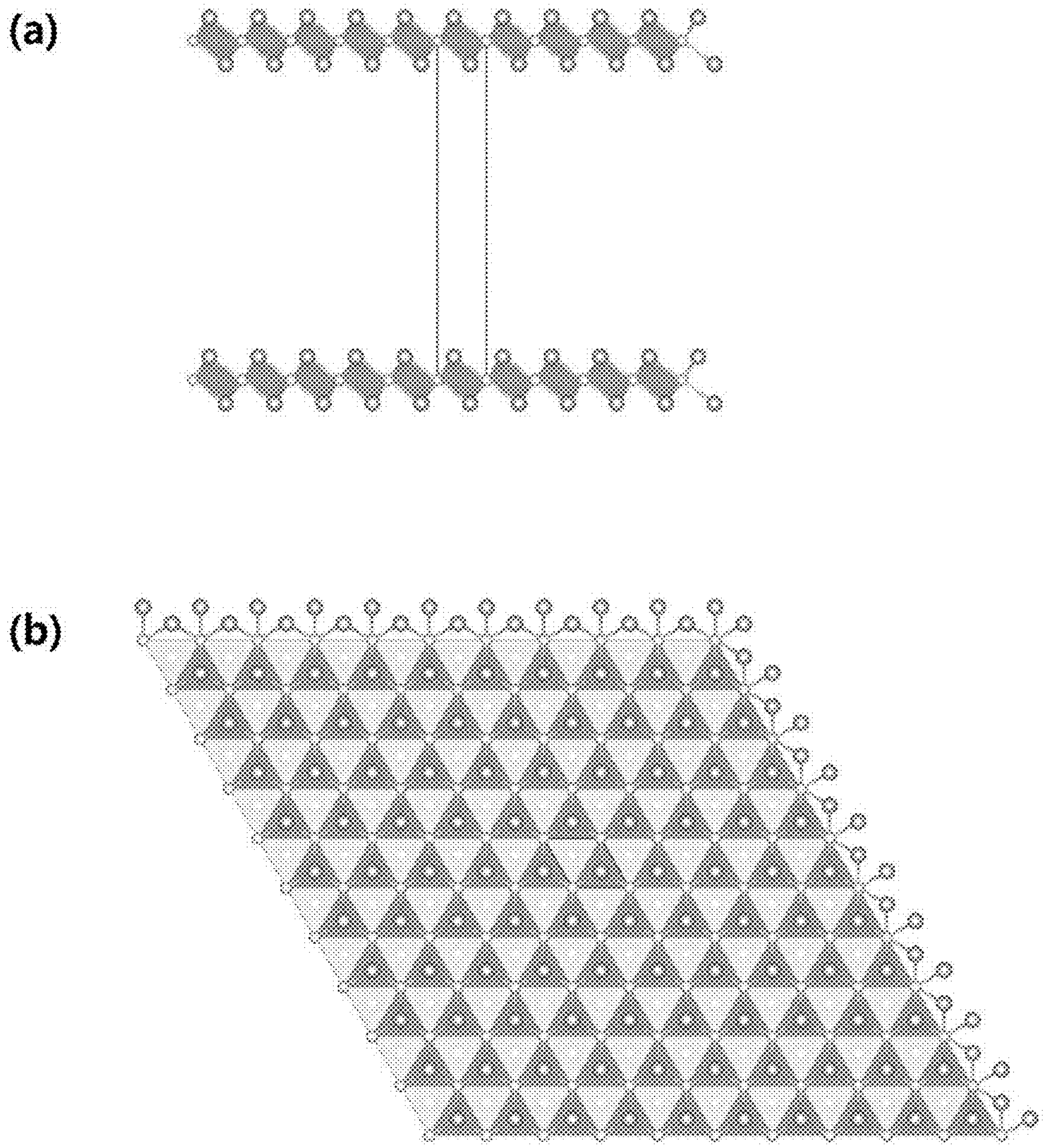
Figure 8:
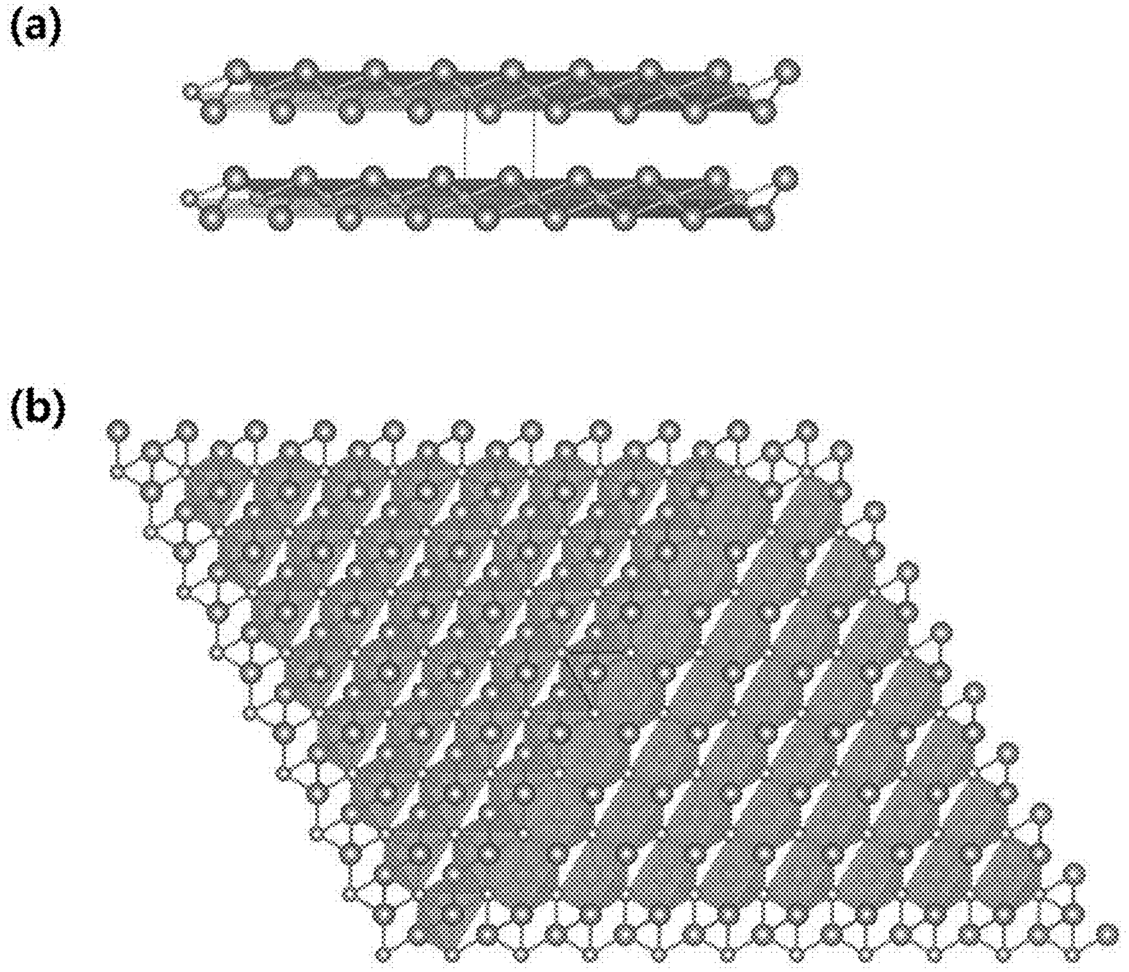

FIGS. 6 to 8 are images depicting the crystal structures of materials derived by a modeling device according to an embodiment of the present invention.

In detail, parts (a) and (b) of FIG. 6 are images of the crystal structure of the new 2D material $Si_2F_8$, which is the first item in the list in FIG. 4, parts (a) and (b) of FIG. 7 are images of the crystal structure of the new 2D material $NbO_2$, which is the second item in the list in FIG. 4, and parts (a) and (b) of FIG. 8 are images of the crystal structure of the new 2D material $Mg_2P$, which is the third item in the list in FIG. 4.

As shown in FIG. 4, $Si_2F_8$ possesses a y-direction elastic modulus exceeding 1000 N/m and has the highest shear modulus among the top 5 materials. $NbO_2$ also exhibits a significantly high y-direction elastic modulus in addition to an x-direction elastic modulus of around 1400 N/m. $Mg_2P$ exhibits isotropy and high values for both elastic modulus and shear modulus.

As described above, the modeling device and method of the present invention makes it possible to generate information about new 2D materials with high structural stability and facilitate the process of deriving such information about new 2D materials.

Additionally, the modeling device and method of the present invention is capable of overcoming the limitations of traditional experimental synthesis methods and property exploration based on post-synthesis analysis and implementing new frameworks for the development of 2D materials, which allows for the rapid exploration of various 2D materials with different characteristics, making it easier to search for materials suitable for commercialization and large-scale production.

Furthermore, the modeling device and method of the present invention can provide structurally stable 2D materials with an average elastic modulus of approximately 700 N/m, indicating their synthesis feasibility.

The present invention with the above configuration is advantageous in terms of being able to generate information on new 2D materials with high structural stability and quickly retrieve information on such new 2D materials.

The present invention is also advantageous in terms of implementing a new 2D material development framework that is capable of overcoming the disadvantages of conventional experimental synthesis methods and property exploration research based on property analysis after synthesis and facilitating search for materials suitable for commercialization and mass production by allowing for quick exploration of 2D materials with various properties.

The present invention is also advantageous in terms of providing structurally stable 2D materials with an average elastic modulus of around 700 N/m and exhibiting synthesis feasibility.

It should be understood that the advantages of the present invention are not limited to the aforesaid but include all advantages that can be inferred from the detailed description of the present invention or the configuration specified in the claims.

The above description of the present invention is for illustrative purposes only, and it will be understood by those skilled in the art that various modifications and changes may be made thereto without departing from the spirit and scope of the invention. Therefore, it should be understood that the embodiments described above are exemplary and not limited in all respects. For example, each component described as a single type may be implemented in a distributed manner, and similarly, components described as distributed may be implemented in a combined form.

The scope of the invention should be determined by the appended claims, and all changes or modifications derived from the meaning and scope of the claims and equivalent concepts thereof should be construed as being included in the scope of the present invention.

DESCRIPTION OF REFERENCE NUMERALS

110: virtual inorganic material generation unit
120: material classification unit
130: space group analysis unit
140: similarity analysis unit
150: new material generation unit
160: property analysis unit
170: display unit

What is claimed is:

1. A device for modeling 2-dimensional (2D) materials using machine learning, the device comprising:

a virtual inorganic material generation unit configured to generate a plurality of virtual inorganic material chemical formulas;

a material classification unit configured to receive data on the plurality of virtual inorganic material chemical formulas from the virtual inorganic material generation unit and classify a 2D material among the plurality of virtual inorganic material chemical formulas into a preliminary 2D material;

a space group analysis unit configured to receive data on the preliminary 2D material from the material classification unit, predict a space group of the preliminary 2D material, and select the preliminary 2D material having a same space group as an existing 2D material as a structurally similar 2D material;

a similarity analysis unit configured to receive data on the structurally similar 2D material from the space group analysis unit and derive the structurally similar 2D material having a chemical composition similar to the existing 2D material as a compositionally similar 2D material;

a new material generation unit configured to receive data on the compositionally similar 2D material from the similarity analysis unit and derive a new 2D material by performing element substitution between chemical formulas of the compositionally similar 2D material and the existing 2D material matching the compositionally similar 2D material; and a property analysis unit configured to receive data on the new 2D material from the new material generation unit and compute thermodynamic stability and mechanical property of the new 2D material, wherein the property analysis unit is configured to perform density functional theory (DFT) calculation on the new 2D material and remove the new 2D material having a negative value for a stiffness tensor among a plurality of types of new 2D materials.

2. The device of claim 1, wherein the virtual inorganic material generation unit generates the plurality of virtual inorganic material chemical formulas using a generative adversarial network (GAN).

3. The device of claim 1, wherein the material classification unit selects the preliminary 2D material using a random forest model.

4. The device of claim 3, wherein the material classification unit trains the random forest model using a virtual material database as predefined material data.

5. The device of claim 1, wherein the space group analysis unit predicts the space group of the preliminary 2D material using a neural network (NN).

6. The device of claim 1, wherein the similarity analysis unit analyzes chemical similarity of the existing 2D material and the structurally similar 2D material using a distance function.

7. The device of claim 6, wherein the distance function is Earth Mover's Distance (EMD) function.

8. The device of claim 1, further comprising a display unit displaying information on the new 2D material received from the property analysis unit on a screen.

9. A method for modeling 2D materials, the method comprising:

generating a plurality of virtual inorganic material chemical formulas;

classifying a 2D material among the plurality of virtual inorganic material chemical formulas into a preliminary 2D material using data on the plurality of virtual inorganic material chemical formulas;

predicting a space group of the preliminary 2D material and selecting the preliminary 2D material having a same space group as an existing 2D material as a structurally similar 2D material;

deriving the structurally similar 2D material having a similar chemical composition to the existing 2D material as a compositionally similar 2D material; deriving a new 2D material by performing element substitution between chemical formulas of the compositionally similar 2D material and the existing 2D material matching the compositionally similar 2D material; and receiving data on the new 2D material and computing thermodynamic stability and mechanical property of the new 2D material, wherein the receiving the data on the new 2D material and the computing includes performing density functional theory (DFT) calculation on the new 2D material and removing the new 2D material having a negative value for a stiffness tensor among a plurality of types of new 2D materials.

* * * * *